(12) United States Patent
Jerger et al.

(10) Patent No.: US 6,264,661 B1
(45) Date of Patent: Jul. 24, 2001

(54) DEVICE FOR DRIVING A WIRE PIN, IN PARTICULAR A KIRSCHNER WIRE, INTO BONE MATERIAL

(75) Inventors: Thomas Jerger, Sindelfingen (DE); Dirk Bernard Van Egmond, Woerden (NL); Thorsten Raabe, Buggensegel (DE)

(73) Assignee: Ferton Holding SA, Delemont (CH)

( * ) Notice: Subject to any disclaimer, the term of this patent is extended or adjusted under 35 U.S.C. 154(b) by 0 days.

(21) Appl. No.: 09/467,921

(22) Filed: Dec. 21, 1999

(30) Foreign Application Priority Data

Dec. 21, 1998 (DE) ............................................. 198 59 135

(51) Int. Cl.[7] .................................................. A61B 17/92
(52) U.S. Cl. ........................................... 606/100; 606/104
(58) Field of Search ..................................... 606/104, 100, 606/99, 86; 173/90, 113, 114, 200, 201, 117, 128, 133

(56) References Cited

U.S. PATENT DOCUMENTS 4,050,528 * 9/1977 Foltz et al. .
4,091,880 * 5/1978 Troutner et al. .
4,298,074   11/1981 Mattchen .
4,441,563 * 4/1984 Walton, II ........................ 606/104 X
5,496,327   3/1996 Den Ouden et al. .

FOREIGN PATENT DOCUMENTS 195 27 529   2/1996 (DE) .
196 18 972   11/1997 (DE) .

\* cited by examiner

*Primary Examiner*—Jeffrey A. Smith
(74) *Attorney, Agent, or Firm*—Griffin & Szipl, P.C.

(57) ABSTRACT

A device for driving a wire pin, and in particular a Kirschner wire, into bone material, comprising a propelling device that acts upon the wire pin which may be inserted into the device from the free front end thereof, said propelling device being driven by periodically repeated impact strokes applied thereupon by an impacting member. The propelling device acts upon the wire pin without any clamping means being involved, which is achieved by the propelling device being designed as a transmitting member against which the free end face of the wire pin may evenly abut and which may transmit the impact strokes of the impacting member as impact pulses into the wire pin through the free end face thereof, with the impact pulses propagating through the wire pin as periodic compression waves so that the wire pin is successively driven into the bone material.

20 Claims, 2 Drawing Sheets

DEVICE FOR DRIVING A WIRE PIN, IN PARTICULAR A KIRSCHNER WIRE, INTO BONE MATERIAL

This application claims priority of German Patent Application Number 198 59 135.7, filed Dec. 21, 1998, the entire disclosure of which is considered to be part of the present disclosure and is specifically incorporated by reference herein.

FIELD OF INVENTION

The present invention relates to a device by means of which an elongated wire pin, in particular a Kirschner wire, may be driven into bone material, comprising a propelling device that acts upon the wire pin which may be inserted into the device from the free front end thereof, said propelling device being moved by an impacting member which generates impact strokes and is in turn periodically moved.

BACKGROUND OF THE INVENTION

A medical instrument for driving a short headed nail into bone material is known from DE 195 27 529 A1. The propelling device described therein is designed as a transmitting piston which is biased by a return spring, and translationally driven by a drive piston. Said drive piston is moved pneumatically in a drive pipe until it abuts against the transmitting piston. The cylindrical, elongated head of the nail is inserted into a guide hole formed in the front end of the device, and pushed into the device until the head abuts against a pin formed at the transmitting piston. The nail is translatorily forced into the bone material by the impact applied upon the transmitting piston by the drive piston.

Devices for driving in a Kirschner wire are used in surgery, in particular for the treatment of bone fractures. The Kirschner wire, which is an elongated wire pin made of metal, for example, may easily and rapidly be driven into the bone portions without causing significant injury to the adjacent soft tissue Such devices are known, for example, from EP 0 597 547 A and DE 27 35 563 A, according to both of which the strokes of the impacting member are transmitted to the wire pin via a receiving sleeve and a clamping device. In the device described in EP 0 597 547, the wire pin is inserted into the device from the rear end thereof, and applied with impact pulses in the form of vibrations which are transmitted via an eccentric clamping device so that the wire is driven to perform an oscillating motion that results in a translatory forward motion thereof. According to DE 27 35 563, the wire is inserted into the front end of the device and clampingly fixed therein. Similar to the operation of a percussion drill, the wire is periodically applied with impact pulses so that it successively advances together with the receiving sleeve, with the other portions of the device being subsequently taken along. The two above described prior art devices must be arranged as close to the bone material as possible so that the wire pin will perform a smooth translatory motion, i.e., the pin does not buckle. To still make sure that a sufficient length of wire material is driven into the bone material, the respective clamping device is designed as a silent ratchet which allows the wire pin to move out of the device, but prevents it from moving back into the device. Thus, the device may contain a sufficient supply of wire material which is successively supplied to be driven into the bone material. Because of their rather complex clamping and gripping devices, said prior art devices are expensive to manufacture. Further, they have a comparatively high energy consumption, which results from the fact that the impacts must be strong enough to move the entire clamping device together with the wire, and that the device must be relatively robust to withstand the extensive mechanical stresses and loads to which it is subjected. Moreover, the impact which may be transmitted to the wire pin itself is rather small.

SUMMARY OF THE INVENTION

The present invention provides a device of the initially mentioned type which may be used for driving a wire pin, in particular a Kirschner wire, into bone material, and which has a simple structure as well as low energy consumption.

In the device according to the present invention, the propelling device acts upon the wire pin without any clamping means being provided. Therefore, the inventive propelling device is designed as a transmission member transmitting elastic impact waves, against which the free end face of the wire pin may evenly abut so that the impact strokes applied by the impacting member are transmitted as periodically repeated impact pulses through the free end face of the wire pin and into the body thereof. Each impact transmitted into the wire pin propagates through the wire pin in the form of a compression wave so that the end thereof facing the bone material is displaced into the bone material, and gets lodged therein so that the rest of the wire pin follows up when the compression wave is being reflected at the bone facing end of the wire pin. Thus, the wire pin projecting from the free front end of the device is periodically and progressively driven into the bone material by periodically successive compression waves. After each impact pulse, the device is moved towards the bone material until the wire pin abuts again at the transmission member so that the device is ready for the next driving process.

According to the present invention and as opposed to conventional devices, the wire pin is driven into the bone material by means of continually applied impact pulses rather than by a translatory motion thereof. Further, the wire pin is not fixed at the propelling device at the time of impact transmission so that complex structures serving to automatically lock and release the wire may be dispensed with. Instead, the end face of the wire loosely abuts against the transmission member at any time of the operational process. As mentioned above, conventional devices have a supply of wire material provided therein which is successively moved out of the device by the propelling device which, during the operation of the device, engages the wire at different portions in the longitudinal direction thereof. In the device according to the present invention, however, the propelling device only engages the end face of the wire pin facing away from the bone material at any time of the process. Even if an elongate or slightly bent wire pin such as a Kirschner wire is used, there is no risk of buckling as the wire pin is not driven into the bone material by a generally translatory motion. The impact pulse transmitted into the wire pin according to the present invention is also able to propagate in the form of a compression wave through an elongate, curved wire pin, and causes the bone-facing end of the wire pin to be displaced into the bone material even if the wire is slightly curved. During each impact pulse, the wire pin is driven into the bone material by a stroke length of approximately 1 mm.

In the device according to the present invention, the transmission member is designed to transmit an impact pulse, into the wire pin and does not, or almost not, perform a translatory motion itself. Thus, no energy is consumed for the acceleration or moving of a clamping device, which results in a reduced energy consumption. The wire pin is formed as a waveguide capable of transmitting elastic longitudinal waves, therefore the impact pulse excites a longitudinal or compression wave in the wire pin which propagates through the wire pin so that the material thereof is locally expanded and compressed. Thus, the free end of the wire is displaced into the bone material by the incident elastic wave. The wave is being attenuated during travelling, and then reflected at the free end of the wire pin so that it causes the free wire portion to contract. However, since the free end portion of the wire is lodged in the bone material and cannot be pulled out thereof, the remaining portion of the wire is caused to follow up the displacement of the free end into the material.

The transmission of impact pulses into an elongate wave transmitting member having the form of a wire is already known from lithotripsy procedures as used, for example, for the crushing of kidney stones. From DE 196 18 972 A1, for example, a device is known wherein an impacting member periodically and repeatedly strikes upon a impact transmitting device which in turn acts upon a wave transmitting member. However, said known device cannot be used to drive a wire pin into bone material because the wire-type wave transmitting member used for crushing the stones is fixed in the device.

The wire pin may be placed at the bone material by hand, similar to the way a nail is held to be beaten in, and the device may be freely positioned by hand at the end face of the wire pin facing towards it. However, the device according to the present invention preferably comprises a guiding sleeve whose guiding hole serves to guidingly receive the headless wire pin so that the latter is freely movable in the longitudinal direction until it abuts against the transmission member. The wire pin is simply inserted into the guiding hole and moved further into said sleeve until it abuts against the transmission member. During operation, the device having the wire inserted therein thus simply has to be pressed against the bone material, and the wire pin may be guided much more precisely by means of the guiding sleeve. In particular, the guiding sleeve is provided at the device in such a way that during its use, the device-facing end portion of the wire pin is inserted into the guiding sleeve so that the wire may be moved towards the transmitting member exactly parallel to the direction of impact transmission, which prevents energy losses during impact transmission to the wire pin. Further, the guiding sleeve prevents the wire pin from buckling during impact transmission, as well as any energy losses resulting therefrom. The transmitting member and the guiding sleeve are not connected with each other to prevent any impact transmission between them so that the transmitting member transmits impacts exclusively to the wire pin, and not to the guiding sleeve.

The transmitting member may be any component, for example a rocker arm, or a bushing which surrounds the wire pin and is open at one side, and is preferably made of a solid material capable of transmitting elastic impact waves, such as a metallic material. Preferably used metallic materials of this type are steel, titanium or alloys thereof, The impacting member may be any component which may be driven to strike upon a working piston, for example a rocker arm or a pivotable plate whose free end strikes upon the transmitting member. Preferably, the impacting member is designed as a drive piston which may be accelerated in a drive pipe. The transmitting member is advantageously formed as a transmitting piston which seals the drive pipe. The piston-shaped design of the impacting member and the transmitting member has the advantage that the drive-side components of the device, which cannot be sufficiently sterilized, may thus be sealed against the wire pin without difficulty so that the contamination of the wire pin is prevented in a simple way. Advantageously, the transmitting piston is elongated so that it has a sufficiently large external surface area for the arrangement of sealing elements. Preferably, the transmitting piston and the drive piston are coaxially arranged so that the transmitting piston may be designed to extend into the drive pipe, which further facilitates the sealing of the drive pipe. In particular when a transmitting piston being provided, it is arranged at an axial distance from the guiding sleeve so that any impact transmission from the transmitting piston to the guiding sleeve is prevented. Further, the motion of the transmitting piston is advantageously limited by stoppers in both axial directions thereof, with a certain axial play being provided so that the impact cannot be transmitted from the transmitting piston to the casing accommodating said piston.

The impacting member may in particular be pneumatically, hydraulically, mechanically or electromagnetically driven. The impacting member may be periodically reciprocated to periodically and repeatedly apply impacts on the transmitting member. Preferably, the impacting member is designed such that it may be driven into the striking direction by any one of the above mentioned driving means, and automatically performs a return motion in the reverse direction, which is achieved by means of a spring, for example.

Although it is possible to arrange the guiding sleeve and the drive-side components such as the impacting member and transmitting member together in one non-divided device, the guiding sleeve is preferably provided in a separate head unit, whereas the transmitting member and the impacting member are arranged in a drive unit. The head unit and the drive unit are corrected to each other by a separable mounting coupling.

The design of the drive-side components and the components holding and guiding the wire pin as separate units enables the parts contacting the wire pin to be sterilized, and kept sterile, without difficulty. For this purpose, the head unit is simply detached from the drive unit so that it is easily accessible for cleaning tools and sterilizing procedures. The drive unit is designed as an independent unit, with the impacting member being encapsulated and sealed by the transmitting member so that once the head unit and the drive unit are assembled, there is no risk of the previously sterilized head unit components being later contaminated.

The device according to the present invention is specifically designed as a manually operated device, therefore it has to be handy and small-sized. However, it has to be sufficiently robust at the same time. Advantageously, the drive unit is provided with an intermediary sleeve at its end portion facing the head unit, which accommodates the transmitting member and onto which the head unit is sealingly threaded or slipped. Furthermore, the drive unit comprises a casing which is threaded or slipped onto the intermediary sleeve so that it is circumferentially flush with the head unit, and in particular sealingly connected there to.

Accordingly, the separable coupling between the head unit and the drive unit is provided by the connection between the head unit and the intermediary sleeve. At its portion facing away from the head unit, the intermediary sleeve may be easily provided with an additional protective casing to surround the drive-side components. However, the transmitting member could also be directly accommodated in a casing member, i.e. without the intermediary sleeve, and the head unit could be directly attached to said casing member, for example. For easy handling, the casing preferably has a tubular shape, and is in particular formed as a cylindrical pipe. Advantageously, the intermediary sleeve comprises an outwardly facing annular flange formed at its longitudinal center, against which both the casing and the head unit sealingly abut. Alternatively, an annular sealing element may be arranged around the intermediary sleeve at a position between the head unit and the casing, which is sealingly compressed between the head unit and the casing.

According to an embodiment of the present invention, the device comprises a friction member which is pressed against the lateral surface of the inserted wire pin and hinders any accidental motion thereof so that the wire pin is prevented from being shot out of the device like a bullet when the device is inadvertently operated. The friction member may, for example, be formed by a suitably designed guiding sleeve whose guiding hole diameter is dimensioned such that it frictionally engages the circumference of the wire but does not prevent the longitudinal displacement of the wire pin within the guiding hole during the insertion thereof. The friction member is preferably formed as an elastic friction member, for example as a rubber element such as a rubber block which is slightly biased against the lateral surface of the wire pin. Preferably, a sealing element is used as a friction member and simultaneously seals the circumference of the inserted wire pin against the device. In this way, the device may be additionally sealed against impurities, and in particular against the infiltration of pathogens. Advantageously, a sealing cap made of plastic material, for example, is used as a sealing element. Said cap is arranged at the wire-outlet end of the device and comprises a through hole through which the wire extends in a sealingly abutting manner. In this way, the device is safely sealed at its wire-outlet end, i.e., at the front end of the device.

To prevent the impacting member from accidentally leaving its starting position, a holding device is provided to hold the impacting member at its starting position. The holding device may be a clamping device, for example, which fixes the impacting member by means of clamping forces which may be overcome by the driving forces. Advantageously, a magnetic holding device is provided to hold the impacting member, and is formed by an electromagnet, for example, but preferably by a permanent magnet. The impacting member may have a magnetic part attached thereto such as a magnetizable metallic member which acts in combination with the magnetic holding device. Preferably, the entire impacting member is made of a magnetizable material such as steel, for example.

The device according to the present invention may be used to drive any type of wire pin, for example also a nail, into any type of material. Its preferred use, however, is for driving a Kirschner wire into bone material. Accordingly, the device is preferably designed for applications as a medical device.

BRIEF DESCRIPTION OF THE DRAWINGS

The present invention will now be explained in more detail by means of preferred embodiments thereof and with reference to the accompanying drawing, wherein.

DETAILED DESCRIPTION OF THE PREFERRED EMBODIMENTS

Figure 1:
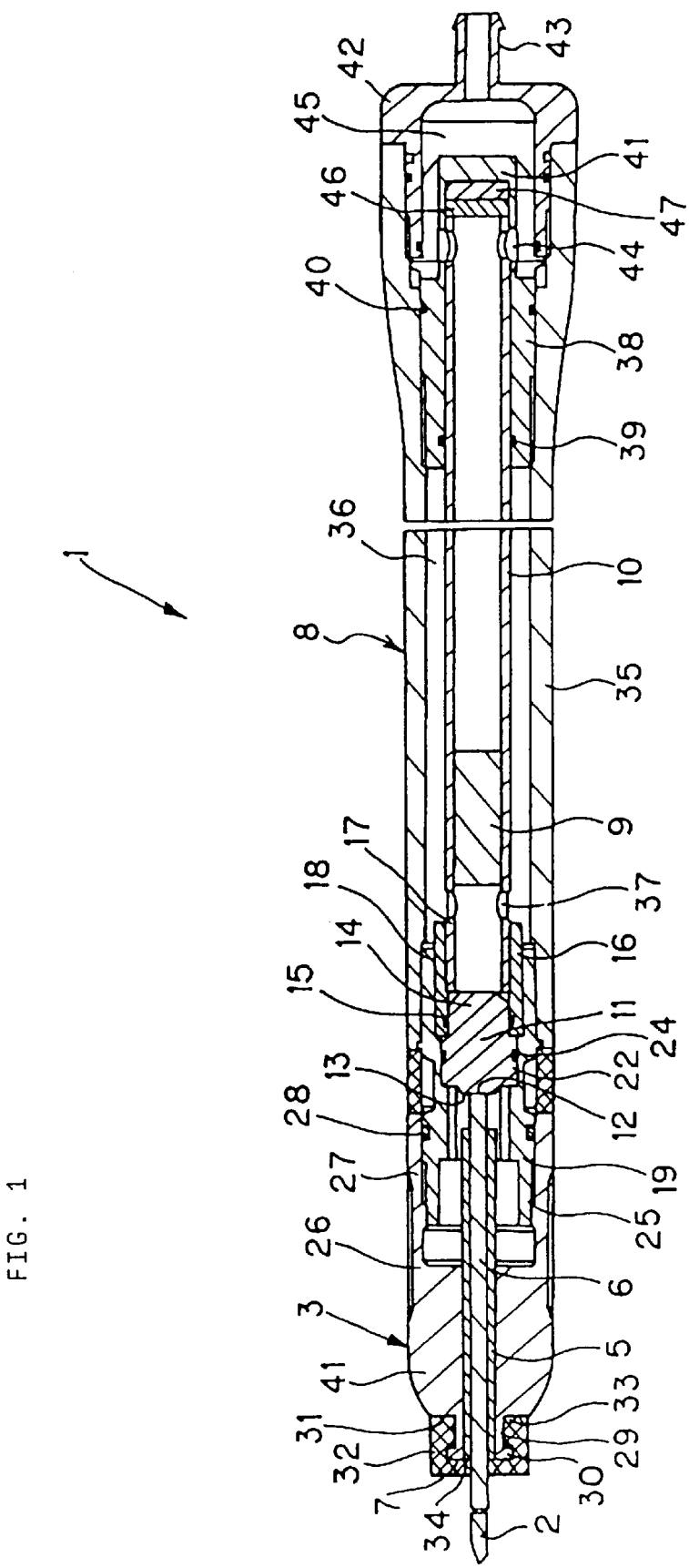
FIG. 1 shows a longitudinal section of an embodiment according to the present invention of a device for driving a wire pin into bone material.
Figure 2:
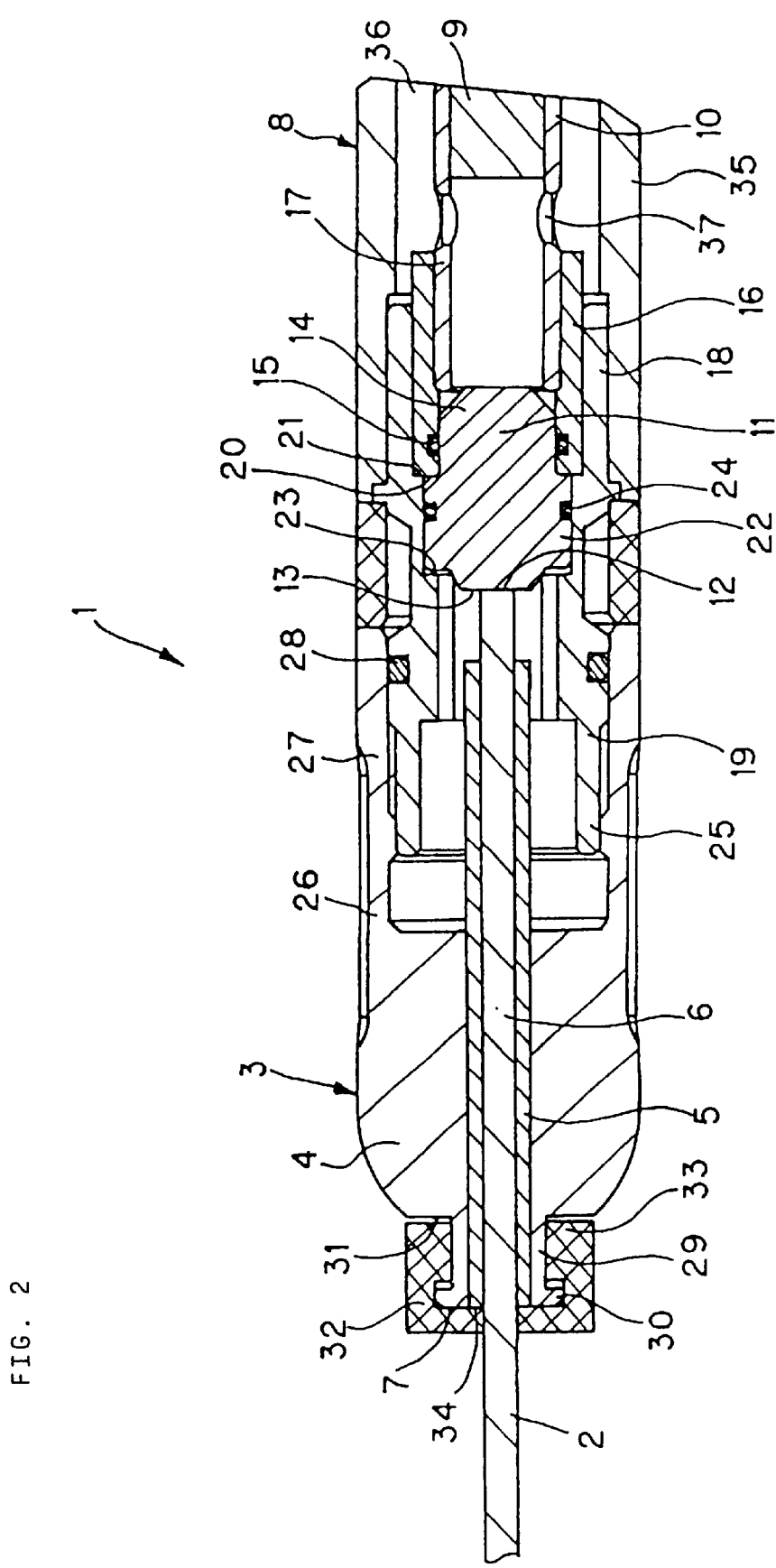
FIG. 2 shows an enlarged view of the front portion of the device according to FIG. 1.

FIGS. 1 and 2 show a longitudinal section of an inventive device 1 for driving a headless, elongated wire pin, and in particular a Kirschner wire 2, into bone material (not shown). The device 1 is designed as a manually operable device and comprises a head unit 3 having a body 4 with openings, and a guiding sleeve 5 which is accommodated in said body 4 and into which an end portion 6 of the Kirschner wire 2 facing away from the bone material is inserted so that a substantial portion of the elongated wire pin or Kirschner wire protrudes from the device. The guiding sleeve 5 extends from the bone material-facing end face 7 of the body 4 across almost the entire length of the head unit 3. As will be explained in more detail later, the head unit 3 is separably attached to a drive unit 8 which comprises an impacting member 9 designed as a cylindrical drive piston which is arranged coaxially with the guide sleeve 5 and received in a cylindrical drive pipe 10 to be freely movable therein so that it may be driven to perform a periodical reciprocating motion.

The drive unit 8 further comprises a transmitting member 11 which is arranged between the impacting member 9 and the guiding sleeve 5 at an axial distance from the guiding sleeve 5, with its end face abutting against the adjacently located end face of the drive pipe 10. The transmitting member 11 has the shape of a piston and forms an axial stop for the Kirschner wire 2 at the end thereof facing away from the bone material. As may be seen from the Figures, the Kirschner wire 2 is inserted into the device 1 from the free front end thereof, and advanced until its end face 12 remote from the bone material evenly abuts against the end face 13 of the transmitting member 11. The piston-shaped transmitting member 11 is arranged to be coaxial with the guiding sleeve 5, and thus to the impacting member 9.

At its end portion 14 facing towards the drive pipe 10, the transmitting member 11 is received in a coupling sleeve 16 almost without radial play so that it is axially guided therein, with the circumference of the transmitting member 11 being sealed by an O-ring 15 accommodated in an inner annular groove formed in the coupling sleeve 16. The coupling sleeve 16 further accommodates the drive pipe 10, i.e. its end portion 17 facing the transmitting member 11, in a sealing manner. For this purpose, said end portion of the drive pipe 10 is inserted into the coupling sleeve 16 so that an outer edge portion of its end face facing the transmitting member 11 abuts against an inner shoulder of the coupling sleeve 16 that forms an axial stop.

The coupling sleeve 16 is accommodated in an end portion 18 facing away from the guiding sleeve 5 of an intermediary sleeve 19 so that an outer edge portion of its guiding sleeve-facing end face 20 abuts against an inner shoulder 21 of the intermediary sleeve 19.

At its end portion 14 facing away from the guiding sleeve 5, the transmitting member 11 comprises an outwardly extending annular flange 22 which is received in the intermediary sleeve 19 almost without radial play and whose axial motion is limited by the inner edge portion of the guiding sleeve-facing end face 20 of the coupling sleeve 16 and an inner shoulder 23 of the intermediary sleeve 19, with a small axial play being provided so that the transmitting member 11 may perform a small axial motion relative to the intermediary sleeve 19 within a range determined by said axial play. The annular flange 22 of the transmitting member 11 is provided with a circumferential annular groove wherein an O-ring 24 is accommodated to seal the circumference of the transmitting member 11 against the intermediary sleeve 19.

At its end portion 25 facing the head unit 3, the intermediary sleeve 19 is provided with an external thread. The body 4 has an annular flange 27 formed at its end portion 26 facing the drive unit 8, which comprises an axially extending internal thread by means of which the body 4, and thus the head unit 3, is sealingly threaded upon the adjacent end portion 26 of the intermediary sleeve 19. The seal between them is formed by an O-ring 28 arranged around the circumference of the intermediary sleeve 19 and accommodated in an annular groove formed in said sleeve 19.

At its end portion 29 facing the bone material during the operation of the device 1, the body 4 is provided with an outer annular groove 31 which is formed by means of a collar 30 arranged at the end face thereof. A cap 32 made of elastic material and provided with an opening as well as with an inwardly extending annular flange 33 to engage into the annular groove 31 is arranged on said end portion 29 of the body 4. The opening in the cap 32 is such that the Kirschner wire 2 inserted into the guiding sleeve 5 extends through the cap 32 in a circumferentially abutting manner. The cap 32 abuts both against the end face 7 of the body 4, and against the end face 34 of the guiding sleeve 5.

The drive unit 8 comprises a cylindrical receiving pipe 35 which serves as a casing accommodating the drive-side components, and is sealingly arranged on the end portion 18 facing away from the head unit 3 of the intermediary sleeve 19, with the drive pipe 10 being received in said receiving pipe 35. An annular chamber 36 is formed between the receiving pipe 35 and the drive pipe 10 and communicates with the interior of the drive pipe 10 via openings 37 formed laterally in the drive pipe 10 at a position adjacent to the coupling sleeve 16.

At its end facing away from the head unit 3, the annular chamber 36 is axially delimited by a sealing bush 38 which surrounds the drive pipe 10 and is axially threaded into the receiving pipe 35. O-rings 39, 40 seal the sealing bush 38 against the drive pipe 10 and the receiving pipe 35.

The end of the drive pipe 10 facing away from the head unit 3 is tightly closed by a cover 41 which simultaneously forms a stopper for the impacting member 9 at the end thereof remote from the transmitting member. The end of the receiving pipe 35 facing away from the head unit 3 is tightly closed by a plug 42 which is formed with a connecting piece 43 for the supply of compressed air. The drive pipe 10 is provided with lateral openings 44 located adjacent to the cover 41 which communicate with the opening in the connecting piece 43 via a chamber 45 formed between the plug 42, the sealing bush 38, the receiving pipe 35 and the drive pipe 10. A rigid plate 46 and an elastic plate 47 are arranged within the cover 41 and act together as an axial buffered stop for the impacting member 9. For this purpose, the two plates 46, 47 are arranged in direct contact with each other, with the rigid plate 46 being closer to the impacting member 9. The elastic plate 47 is made of an elastic plastic material or of rubber and serves as a buffer element. The rigid plate 46 is made of a permanent-magnetic material, i.e., it forms a permanent magnet. The impacting member 9 is made of a magnetizable material such as steel. The rigid plate 46 thus forms a magnetic holding device for the impacting member 9 at which the impacting member 9 is held at its starting position so that it is fixed against accidental movement. The magnetic forces created between the rigid plate 46 and the impacting member 9 are dimensioned such that they may be overcome by the driving forces.

Next, the operation of the inventive device 1 for driving in a Kirschner wire 2 will now be explained. First, the Kirschner wire 2 is inserted into the guiding sleeve 5 provided in the head unit 3 until its end face abuts against the transmitting member 11. Next, the device 1, and thus the bone material-facing end of the Kirschner wire 2, are pressed against the bone material. In this way, it is ensured that the annular flange 22 of the transmitting member 11 is pressed against the coupling sleeve 16 so that the axial play between the annular flange 22 and the head unit-facing shoulder 23 of the intermediary sleeve 19, which is necessary for an adequate impact transmission to the Kirschner wire 2, is ensured as well.

The device 1 is periodically supplied with compressed air through the connecting piece 43 so that the Kirschner wire 2 may be driven into the bone material. Via the chamber 45 and the openings 44, the compressed air enters the interior of the drive pipe 10 where it accelerates the impacting member 9 towards the transmitting member 11, i.e., to the left according to the Figures. The air which is displaced from the drive pipe 10 by the impacting member 9 is forced through the openings 37 and into the annular chamber 36. The impacting member 9 is accelerated by means of the compressed air supplied through the connecting piece 43 until it abuts against the transmitting member 11. After impacting upon the transmitting member 11, the impacting member 9 is moved back, i.e., in the reverse direction, by the air compressed in the annular chamber 36 and flowing back through the openings 37 and into the drive pipe 10, until it abuts against the cover 41 acting as a stop. Next, compressed air is again supplied through the connecting piece 43 so that the above described drive cycle may be repeated.

When the impacting member 9 abuts against the transmitting member 11, it transmits an impact pulse thereupon which is transmitted further to the Kirschner wire 2 abutting against the transmitting member 11. Preferably, a compression wave is excited in the transmitting member 11 and then transmitted to the Kirschner wire 2 The axial play between the annular flange 22 of the transmitting member 11 and the inner shoulder 23 of the intermediary sleeve 19 prevents the impact from being transmitted to the intermediary sleeve 19. The axial play between the transmitting member 11 and the guiding sleeve 5 accommodating the Kirschner wire 2 ensures that the entire impact pulse is transmitted to the Kirschner wire 2 rather than to the guiding sleeve 5. The elongate guiding sleeve 5 ensures that the transmitting member-facing end portion 6 of the Kirschner wire 2 is kept straight so that energy losses caused by an impact transmission to a bent wire are prevented. The impact pulse, or preferably the compression wave, propagates through the Kirschner wire 2 so that the bone material-facing end thereof is displaced into the bone material. The end of the Kirschner wire 2 which has been displaced into the bone material remains lodged therein because the impact pulse reflected at this end of the wire is dampened to such an extent that it cannot cause any reverse displacement of the wire end, i.e. a displacement thereof out of the bone material. The lodged end of the Kirschner wire 2 causes the remaining portion thereof to follow up automatically. As a result, a small gap is formed between the end face 12 of the Kirschner wire 2 which is remote from the bone material and the end face 13 of the transmitting member 11, which gap is immediately closed since the entire device 1 is continuously pressed towards the direction in which the Kirschner wire 2 is driven in so that the end face 12 of the wire will always abut against the intermediary member 11.

Thus, when the device 1 is continuously moved in the direction in which the wire 2 is to be driven in, the Kirschner wire 2 is driven into the bone material by periodically repeated impact strokes of the impacting member 9 acting upon the transmitting member 11 which is in constant abutment with the adjacent end face 12 of the Kirschner wire 2.

The cap 32 has a dual function: it both seals the device 1 against the Kirschner wire 2 and forms a friction member which abuts against the Kirschner wire so that, if the device 1 is accidentally operated, the wire is prevented from shooting out of the device 1 and possibly causing injury to nearby persons, because the translatory motion of the wire is controlled by the frictionally abutting cap 32.

What is claimed is:

1. A device for driving an elongated wire pin into bone material, comprising:
    a propelling device actable upon the wire pin when a front free end of the pin is inserted into the device, said propelling device being driven by periodically repeated impact strokes applied thereupon by a periodically driven impacting member,
    wherein the propelling device acts upon the inserted wire pin without any clamping means, and
    wherein the propelling device further comprises a transmitting member which transmits elastic impact waves to the wire pin when the free end of the inserted wire pin evenly abuts the transmitting member, the transmitting member transmitting the impact strokes of the impacting member as periodical impact pulses into the wire pin through the free end of the wire pin so that each impact pulse propagates through the wire pin in the form of a compression wave, whereby the wire pin protruding from a front end of the device is periodically and progressively drivable into the bone material.

2. A device according to claim 1, further comprising a guiding sleeve for guidingly receiving the wire pin so that the wire pin is movable in a longitudinal direction until the wire pin abuts against the transmitting member.

3. A device according to claim 2, wherein the guiding sleeve is provided in a head unit of the device, that the transmitting member and the impacting member are provided in a drive unit of the device, and that the head unit and the drive unit are mounted to each other by a separable mounting coupling.

4. A device according to claim 3, wherein the drive unit comprises an intermediary sleeve at an end portion facing the head unit, wherein the transmitting member is received in the intermediate sleeve, and wherein the head unit is threaded onto the intermediary sleeve in a sealing manner, and wherein the drive unit further comprises a casing attached to the intermediary sleeve so that the casing is circumferentially flush with the head unit.

5. A device according to claim 2, wherein the guiding sleeve is arranged at an axial distance from the transmitting member.

6. A device according to claim 1, wherein the impacting member is a drive piston periodically acceleratable in an drive pipe, and wherein the transmitting member is a transmitting piston which seals the drive pipe.

7. A device according to claim 1, further comprising a friction member disposed to be pressed against a lateral surface of a wire pin inserted in the device.

8. A device according to claim 7, wherein the friction member is an elastic friction member and a sealing member which sealingly surrounds the circumference of the inserted wire pin.

9. A device according to claim 8, wherein the sealing member is a sealing cap arranged at a wire-outlet end of the device so that the inserted wire pin extends through the sealing cap in a sealed manner.

10. A device according to claim 1 adapted to drive a Kirschner wire into bone material.

11. A device for driving an elongated wire pin into bone material, comprising:
    a head unit, including:
        a body having a front face and an opening for receiving a wire pin, and
        a guiding sleeve disposed in said body for receiving and guiding the wire pin without clamping; and
    a drive unit, including
        a drive pipe disposed co-axially with the guiding sleeve of the head unit,
        an impacting member reciprocatingly disposed within the drive pipe, and
        a transmitting member arranged co-axially between the impacting member and the guiding sleeve, so that, when a wire pin is inserted in the guiding sleeve to abut the transmitting member, and the impacting member is reciprocated in the drive pipe, a compression wave is transmitted to the wire pin to drive the wire pin.

12. A device according to claim 11, wherein the head unit is separably attached to the drive unit.

13. A device according to claim 11, further comprising a coupling sleeve containing said transmitting member almost without radial play so that the transmitting member is axially guided in the coupling sleeve, the coupling sleeve sealingly coupling the drive pipe to the transmitting member.

14. A device according to claim 13, wherein the drive unit further comprises:
    a receiving pipe, wherein the drive pipe is disposed within the receiving pipe and an annular chamber is defined between the drive pipe and the receiving pipe;
    an intermediary sleeve receiving the transmitting member and limiting the axial motion of the transmitting member;
    wherein the drive pipe comprises an opening at a position adjacent to the coupling sleeve to allow communication between an interior of the drive pipe and the annular space;
    a connecting piece for attachment to a source of compressed air, connected to the interior of the drive pipe to drive the impacting member toward the transmitting member within the drive pipe when compressed air is supplied to the connecting piece.

15. The device according to claim 14, wherein the transmitting member further comprises an annular flange disposed to engage said intermediary flange to limit the axial motion of the transmitting member.

16. The device according to claim 14, wherein the drive unit further comprises a rigid plate facing the impacting member at an end of the drive pipe distal from the transmitting member and a elastic plate on a side of the rigid plate facing away from the transmitting member, wherein the plates serve to stop the axial motion of the impacting member within the drive pipe.

17. The device according to claim 16, wherein the rigid plate and the impacting member are made of magnetizable material and attract one another.

18. The device according to claim 11, further comprising:
    a cap connected to the front face of the body and having an opening contiguous with the guiding sleeve and through which the wire pin insertable.

19. The device according to claim 18, wherein said cap is an elastic friction member disposed to frictionally engage an inserted wire pin.

20. The device according to claim 11, wherein the impacting member is a cylindrical drive piston.

* * * * *